United States Patent
Konda et al.

(10) Patent No.: US 9,828,331 B2
(45) Date of Patent: Nov. 28, 2017

(54) TETRAHYDRO-ISOHUMULONE DERIVATIVES, METHODS OF MAKING AND USING

(71) Applicant: KINDEX PHARMACEUTICALS, INC., Seattle, WA (US)

(72) Inventors: Veera Konda, Bellevue, WA (US); Jan Urban, Port Orchard, WA (US); Anuradha Desai, Bellevue, WA (US); Clinton J. Dahlberg, Port Orchard, WA (US); Brian J. Carroll, Gig Harbor, WA (US)

(73) Assignee: KINDEX PHARMACEUTICALS, INC., Seattle, WA (US)

(*) Notice: Subject to any disclaimer, the term of this patent is extended or adjusted under 35 U.S.C. 154(b) by 0 days.

(21) Appl. No.: 14/593,164

(22) Filed: Jan. 9, 2015

(65) Prior Publication Data

US 2015/0119461 A1 Apr. 30, 2015

Related U.S. Application Data

(63) Continuation of application No. PCT/US2013/049788, filed on Jul. 9, 2013.

(60) Provisional application No. 61/669,441, filed on Jul. 9, 2012.

(51) Int. Cl.

| | | |
|---|---|---|
| C07C 225/14 | (2006.01) | |
| A61K 31/122 | (2006.01) | |
| A61K 31/135 | (2006.01) | |
| C07C 59/90 | (2006.01) | |
| C07C 69/02 | (2006.01) | |
| C07C 69/22 | (2006.01) | |
| C07C 69/614 | (2006.01) | |
| C07C 69/78 | (2006.01) | |
| C07C 69/96 | (2006.01) | |
| C07C 69/28 | (2006.01) | |
| C07C 69/612 | (2006.01) | |
| C07C 49/707 | (2006.01) | |
| C07C 49/743 | (2006.01) | |
| C07C 251/42 | (2006.01) | |

(52) U.S. Cl.
CPC .......... *C07C 225/14* (2013.01); *A61K 31/122* (2013.01); *A61K 31/135* (2013.01); *C07C 49/707* (2013.01); *C07C 49/743* (2013.01); *C07C 59/90* (2013.01); *C07C 69/02* (2013.01); *C07C 69/22* (2013.01); *C07C 69/28* (2013.01); *C07C 69/612* (2013.01); *C07C 69/614* (2013.01); *C07C 69/78* (2013.01); *C07C 69/96* (2013.01); *C07C 251/42* (2013.01); *C07C 2601/08* (2017.05); *C07C 2601/10* (2017.05)

(58) Field of Classification Search
USPC ........................................ 514/512, 573, 690
See application file for complete search history.

(56) References Cited

U.S. PATENT DOCUMENTS 8,410,178 B2 * 4/2013 Carroll ................ A61K 31/122
514/690
2004/0086580 A1 5/2004 Tripp et al.
2010/0222262 A1 * 9/2010 Konda .................. C07C 49/707
514/2.4
2011/0117252 A1 5/2011 Buffin et al.
2011/0257074 A1 10/2011 Carroll et al.
2012/0108671 A1 5/2012 Carroll et al.

FOREIGN PATENT DOCUMENTS

WO 2005084680 A1 9/2005
WO 2008140842 A1 11/2008

OTHER PUBLICATIONS

Berge, S. M., et al., "Pharmaceutical Salts," J. Pharm. Sci. 66(1):1-19 (1977).
Dahlberg, C. J., et al., "Countercurrent Purification of the Tetrahydro Iso-Alpha Acids Derived from *Humulus lupulus* L.," J. Sep. Sci. 33:2828-2832 (2010).
Dahlberg, C. J., et al., "Isolation of Bitter Acids from Hops (*Humulus lupulus* L.) Using Countercurrent Chromatography," J. Sep. Sci. 35:1183-1189 (2012).
Desai, A., et al., "META060 Inhibits Multiple Kinases in the Nf-kB Pathway and Suppresses LPS-Mediated Inflammation In Vitro and Ex Vivo," Inflamm. Res. 58:229-234 (2009).
Everard, A., et al., "Tetrahydro iso-Alpha Acids from Hops Improve Glucose Homeostasis and Reduce Body Weight Gain and Metabolic Endotoxemia in High-Fat Diet-Fed Mice," PLoS One 7(3):e33858 (2012).
Hall, A. J., et al., "Safety, Efficacy and Anti-Inflammatory Activity of Rho Iso-Alpha-Acids from Hops," Phytochem. 69:1534-1547 (2008).
Khatib, A., et al., "Isolation of Individual Hop Iso-Alpha-Acids Stereoisomers by Beta-Cyclodextrin," Food Chem. 119:354-357 (2010).
Konda, V. R., et al., "META060 Inhibits Osteoclastogenesis and Matrix Metalloproteinases In Vitro and Reduces Bone and Cartilage Degradation in a Mouse Model of Rheumatoid Arthritis," Arthritis Rheum. 62(6):1683-1693 (2010).
Ting, P. L.P., et al., "Preparation and Purification of Hop Acids and Their Derivatives," J. Am. Soc. Brew. Chem. 54(2):103-109 (1996).
Tripp, M. L., et al., "Rho-Iso-Alpha Acids and Tetrahydro-Iso-Alpha Acids Are Selective Protein Kinase Inhibitors which Potently Reduce Inflammation in Macrophages In Vitro and in the Collagen-Induced Rheumatoid Arthritis Model In Vivo," Acta Hort. (ISHS) 848:221-233 (2009).
U.S., International Search Report and Written Opinion dated Dec. 20, 2013 for PCT/US2013/049788.
U.S., International Preliminary Report on Patentability dated Jun. 26, 2014 for PCT/US2013/049788.
European Patent Office, Supplementary Partial European Search Report dated Mar. 9, 2016 for European Patent Application No. 13817170.7.
International Patent Office, Office Action for JP Patent Application No. 2015-521755, dated May 23, 2017. 11 Pages.

* cited by examiner

*Primary Examiner* — Pancham Bakshi
(74) *Attorney, Agent, or Firm* — Perkins Coie LLP; Patrick D. Morris

(57) ABSTRACT

The present application provides novel tetrahydro-isohumulone (THIAA) derivatives and substantially enantiomerically pure compositions and pharmaceutical formulations thereof. The application further provides methods of using the disclosed compounds and compositions to activate PPARγ, inhibit inflammation, and treat conditions associated with inflammation and conditions responsive to PPARγ modulation such as diabetes.

1 Claim, No Drawings

TETRAHYDRO-ISOHUMULONE DERIVATIVES, METHODS OF MAKING AND USING

PRIORITY CLAIM

This application is a continuation of International Application Number PCT/US2013/049788, filed Jul. 9, 2013, which claims priority to U.S. Provisional Application No. 61/669,441, filed Jul. 9, 2012, the disclosure of which is incorporated by reference herein in its entirety.

BACKGROUND

Hops (*Humulus lupulus* L.) is a plant that has been used for medicinal purposes for centuries and is currently used in the brewing industry. Hops contains both alpha acids (humulones) and beta acids (lupulones). Alpha acids/humulones have the general structure:

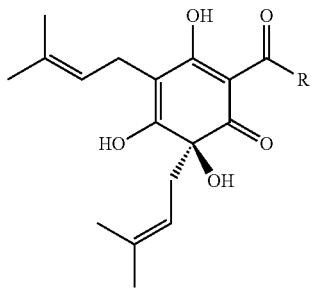

Formula I

The three primary types of alpha acids are humulone (R=CH$_2$CH(CH$_3$)$_2$), cohumulone (R=CH(CH$_3$)$_2$), and adhumulone (R=CH(CH$_3$)CH$_2$CH$_3$). There are also two less common alpha acids in hops, prehumulone and posthumulone. Alpha acids can be converted to cis or trans iso-alpha acids/isohumulones by heat-induced isomerization of alpha acids, and these iso-alpha acids can in turn converted to cis or trans reduced iso-alpha acids by hydrogenation. The three primary types of reduced iso-alpha acids are dihydro- (also known as rho-), tetrahydro-, and hexahydro-iso-alpha acids (RIAA, THIAA, and HIAA, respectively).

Several compounds derived from hops have been found to possess anti-inflammatory activity (Hall 2008; Desai 2009; Tripp 2009; Konda 2010). THIAA extracts have been shown to inhibit inflammation (Desai 2009), reduce symptoms of arthritis in a mouse model of collagen-induced arthritis (Konda 2010), and improve glucose homeostasis in a high fat diet-induced metabolic endotoxemia model (Everard 2012). In each of these cases, the THIAA compounds shared a substituted 1,3-cyclopentadione motif.

The first attempts to identify the stereochemical configuration of the alpha acids and their derivatives were incorrect, starting with the alpha acids (which naturally have (−) optical rotation) and continuing through to the isomerized alpha acids. The alpha acids were originally given the 6R configuration, but are now known to be 6S. The correct stereochemical configuration was identified in U.S. Patent Publication No. 2012/0108671, which disclosed the stereochemical configuration of the THIAA cis 3,4-dihydroxy-2-(3-methylbutanoyl)-5-(3-methylbutyl)-4-(4-methylpentanoyl)cyclopent-2-en-1-one ("KDT500," also known as cis tetrahydro isohumulone) based on X-ray crystallography data. There are two enantiomers of KDT500: (+)-(4S,5R)-3,4-dihydroxy-2-(3-methylbutanoyl)-5-(3-methylbutyl)-4-(4-methylpentanoyl)cyclopent-2-en-1-one ("(+)-KDT500") and (−)-(4R,5S)-3,4-dihydroxy-2-(3-methylbutanoyl)-5-(3-methylbutyl)-4-(4-methylpentanoyl)cyclopent-2-en-1-one ("(−)-KDT500"). The structures of (+)-KDT500 and (−)-KDT500 are set forth in Formulas II and III, respectively.

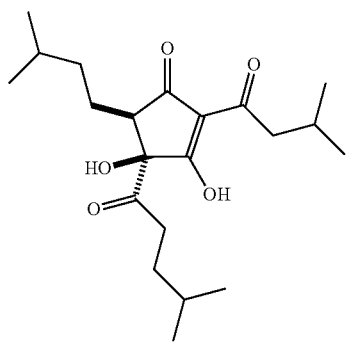

Formula II

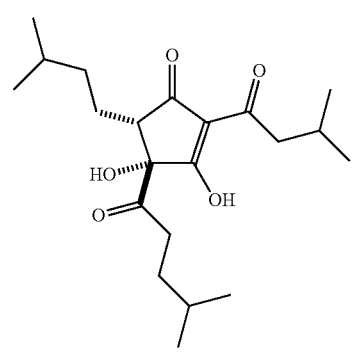

Formula III

U.S. Patent Publication No. 2012/0108671 describes the purification and characterization of KDT500 and its potassium salt KDT501. An enriched THIAA extract containing predominantly the cis diastereomers was obtained during hops processing and purified using countercurrent chromatography (CCC), and the isolated (+)-KDT500 was converted to (+)-KDT501 by reacting with 1 equivalent of potassium salt (e.g., KOH).

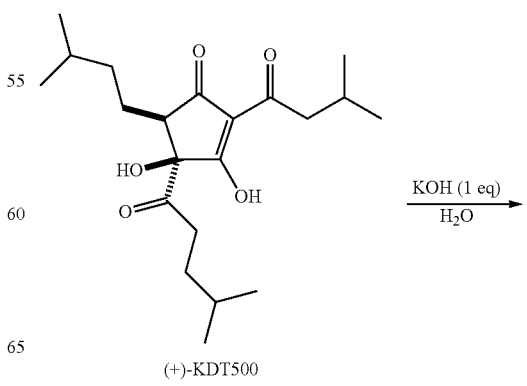

(+)-KDT500

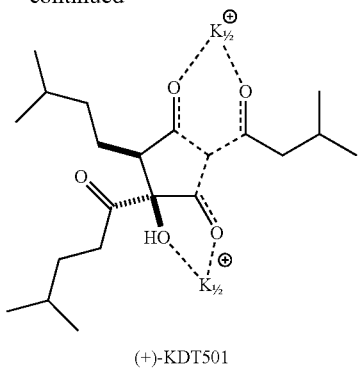

(+)-KDT501

(+)-KDT501 was found to exhibit both anti-inflammatory and anti-diabetic effects.

SUMMARY

Provided herein in certain embodiments are novel THIAA derivatives, as well as enantiomerically pure compositions and pharmaceutical compositions comprising these derivatives. In certain embodiments, the THIAA derivatives provided herein are selected from KDT100, KDT700, KDT0005, KDT0017, KDT0020, KDT0024, KDT0033, KDT0034, KDT0035, KDT0036, KDT0037, KDT0038, KDT0039, KDT0040, KDT0001/2, KDT0041, KDT0042, and KDT0043 or salts or crystals thereof. In certain embodiments, salts of the THIAA derivatives disclosed herein may be inorganic or organic salts, including but not limited to potassium, aluminum, calcium, copper, guanidinium, iron, lithium, magnesium, sodium, zinc, cinchonidine, cinchonine, and diethanolamine salts.

Provided herein in certain embodiments are methods of synthesizing the novel THIAA derivatives disclosed herein. In certain embodiments, these synthesis methods utilize one or more of the acylation, enamine, oxime, and reduction protocols set forth herein.

Provided herein in certain embodiments are methods of activating PPARγ either selectively or in combination with PPARα and methods of decreasing levels of one or more inflammatory markers in vitro or in vivo using one or more of the THIAA derivatives or compositions thereof provided herein. In certain embodiments, the composition is a substantially enantiomerically pure pharmaceutical composition comprising a THIAA derivative and one or more pharmaceutically acceptable carriers. In certain embodiments, the methods are used to treat a condition associated with decreased PPARγ activity in a subject in need thereof.

Provided herein in certain embodiments are methods of inhibiting inflammation, treating a condition associated with inflammation, activating PPARγ either selectively or in combination with PPARα, treating a condition responsive to PPARγ modulation, or decreasing levels of one or more inflammatory markers in a subject in need thereof by administering to the subject a therapeutically effective amount of one or more of the THIAA derivatives or compositions thereof provided herein. In certain of these embodiments, the derivatives are administered via a substantially enantiomerically pure pharmaceutical composition as provided herein. In certain embodiments, the condition responsive to PPARγ modulation is type II diabetes, obesity, hyperinsulinemia, metabolic syndrome, non alcoholic fatty liver disease, non alcoholic steatohepatitis, an autoimmune disorder, or a proliferative disorder. Similarly, in certain embodiments the condition associated with inflammation is diabetes.

DETAILED DESCRIPTION

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

As disclosed herein, a novel set of THIAA derivatives have been synthesized and analyzed for their ability to treat inflammatory conditions and diabetes. These derivatives are summarized in Table 1. Provided herein in certain embodiments are these THIAA derivatives and salts and crystals thereof, including crystals of the salts. Also provided herein are compositions comprising these derivatives and salts and crystals thereof, including substantially enantiomerically pure compositions.

TABLE 1

| Compound name | MW | Structure | Chemical name |
|---|---|---|---|
| (+)-KDT500 | 366 | 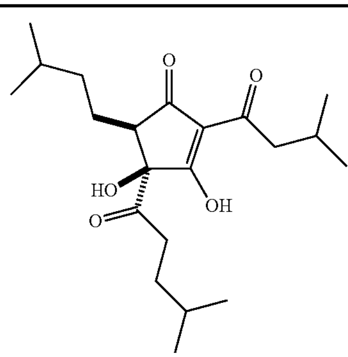 | (+)-(4S,5R)-3,4-dihydroxy-2-(3-methylbutanoyl)-5-(3-methylbutyl)-4-(4-methylpentanoyl)cyclopent-2-en-1-one |

TABLE 1-continued

THIAA derivatives:

| Compound name | MW | Structure | Chemical name |
|---|---|---|---|
| (+)-KDT501 | 404 | 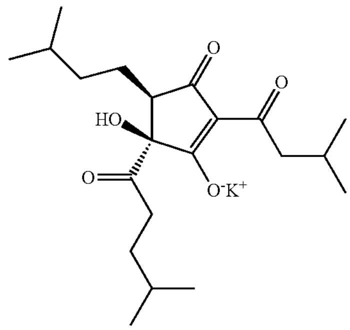 | Potassium salt of (+)-KDT500 |
| (+)-KDT100 (Example 16) | 342 | 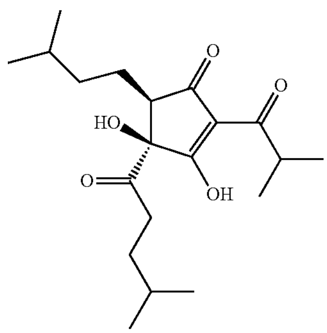 [SMILES: CC(C)CCC(=O)[C@@]1(O)C(O)=C(C(=O)C(C)C)C(=O)[C@@H]1CCC(C)C] | (4S,5R)-3,4-dihydroxy-5-(3-methylbutyl)-4-(4-methylpentanoyl)-2-(2-methylpropanoyl)cyclopent-2-en-1-one |
| (+)-KDT700 (Example 18) | 366 | 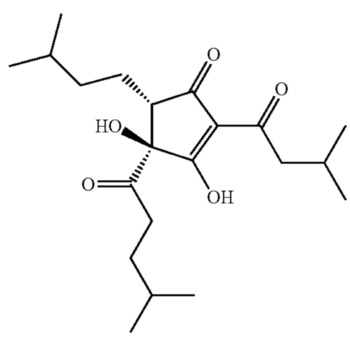 [SMILES: CC(C)CCC(=O)[C@@]1(O)C(O)=C(C(=O)CC(C)C)C(=O)[C@H]1CCC(C)C] | (4S,5S)-3,4-dihydroxy-2-(3-methylbutanoyl)-5-(3-methylbutyl)-4-(4-methylpentanoyl)cyclopent-2-en-1-one |
| KDT0005 (Example 13) | 397 | 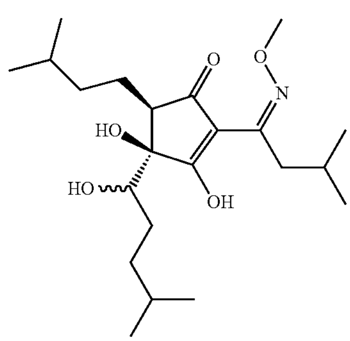 [SMILES: CO/N=C(/CC(C)C)C1=C(O)[C@](O)(C(O)CCC(C)C)[C@@H](CCC(C)C)C1=O] | (4R,5R)-3,4-dihydroxy-4-(1-hydroxy-4-methylpentyl)-2-(N-methoxy-3-methylbutanimidoyl)-5-(3-methylbutyl)cyclopent-2-en-1-one |

TABLE 1-continued

THIAA derivatives:

| Compound name | MW | Structure | Chemical name |
|---|---|---|---|
| KDT0017 (Example 10) | 409 | 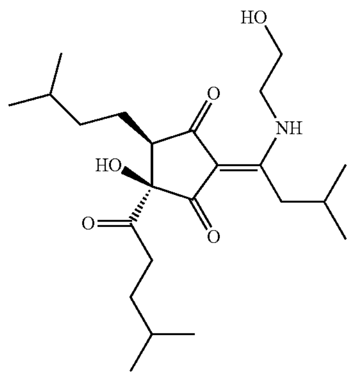 [SMILES: CC(C)CCC(=O)[C@@]1(O)C(=O)/C(=C(\CC(C)C)NCCO)C(=O)[C@@H]1CCC(C)C] | (4R,5R)-4-hydroxy-2-{1-[(2-hydroxyethyl)amino]-3-methylbutylidene}-5-(3-methylbutyl)-4-(4-methylpentanoyl)cyclopentane-1,3-dione |
| KDT0020 (Example 9) | 379 | 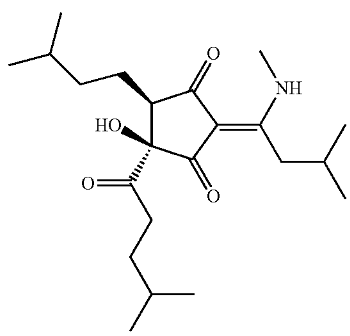 [SMILES: CN/C(CC(C)C)=C1\C(=O)[C@H](CCC(C)C)[C@@](O)(C(=O)CCC(C)C)C1=O] | (4R,5R)-4-hydroxy-5-(3-methylbutyl)-2-[3-methyl-1-(methylamino)butylidene]-4-(4-methylpentanoyl)cyclopentane-1,3-dione |
| KDT0024 (Example 11) | 455 | 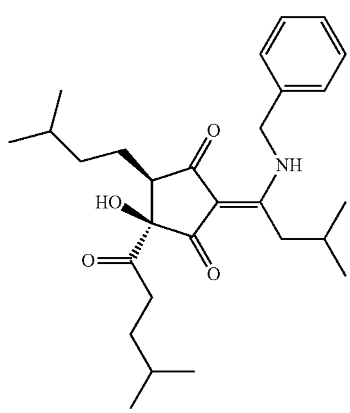 [SMILES: CC(C)CCC(=O)[C@@]1(O)C(=O)/C(=C(\CC(C)C)NCc2ccccc2)C(=O)[C@@H]1CCC(C)C] | (4R,5R)-2-[1-(benzylamino)-3-methylbutylidene]-4-hydroxy-5-(3-methylbutyl)-4-(4-methylpentanoyl)cyclopentane-1,3-dione |
| KDT0033 (Example 3) | 450 | 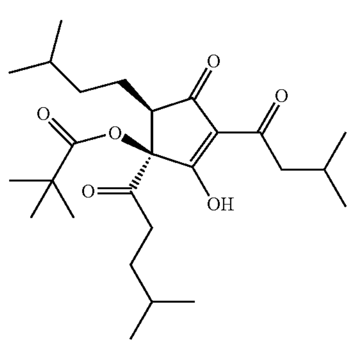 [SMILES: CC(C)CCC(=O)[C@@]1(OC(=O)C(C)(C)C)C(O)=C(C(=O)CC(C)C)C(=O)[C@@H]1CCC(C)C] | (1S,5R)-2-hydroxy-3-(3-methylbutanoyl)-5-(3-methylbutyl)-1-(4-methylpentanoyl)-4-oxocyclopent-2-en-1-yl 2,2-dimethylpropanoate |

TABLE 1-continued

THIAA derivatives:

| Compound name | MW | Structure | Chemical name |
|---|---|---|---|
| KDT0034 (Example 2) | 464 | 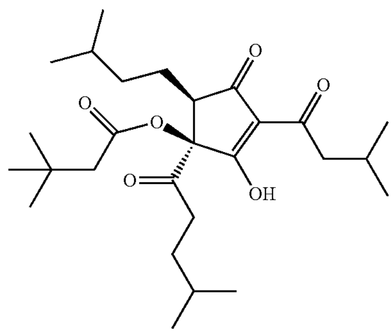 [SMILES: CC(C)CCC(=O)[C@@]1(OC(=O)CC(C)(C)C)C(O)=C(C(=O)CC(C)C)C(=O)[C@@H]1CCC(C)C] | (1S,5R)-2-hydroxy-3-(3-methylbutanoyl)-5-(3-methylbutyl)-1-(4-methylpentanoyl)-4-oxocyclopent-2-en-1-yl 3,3-dimethylbutanoate |
| KDT0035 (Example 4) | 462 | 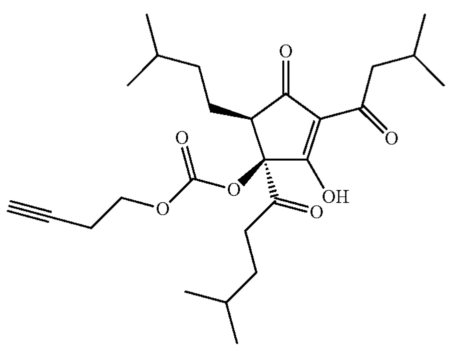 [SMILES: C#CCCOC(=O)O[C@]1(C(=O)CCC(C)C)C(O)=C(C(=O)CC(C)C)C(=O)[C@@H]1CCC(C)C] | but-3-yn-1-yl (1S,5R)-2-hydroxy-3-(3-methylbutanoyl)-5-(3-methylbutyl)-1-(4-methylpentanoyl)-4-oxocyclopent-2-en-1-yl carbonate |
| KDT0036 (Example 1) | 506 | 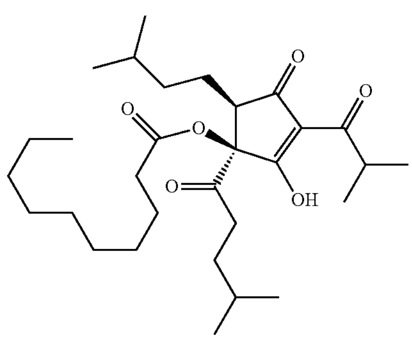 [SMILES: CCCCCCCCCC(=O)O[C@]1(C(=O)CCC(C)C)C(O)=C(C(=O)C(C)C)C(=O)[C@@H]1CCC(C)C] | (1S,5R)-2-hydroxy-5-(3-methylbutyl)-1-(4-methylpentanoyl)-3-(2-methylpropanoyl)-4-oxocyclopent-2-en-1-yl decanoate |
| KDT0037 (Example 5) | 452 | 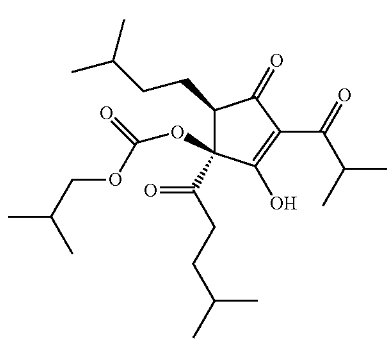 [SMILES: CC(C)CCC(=O)[C@@]1(OC(=O)OCC(C)C)C(O)=C(C(=O)C(C)C)C(=O)[C@@H]1CCC(C)C] | (1S,5R)-2-hydroxy-5-(3-methylbutyl)-1-(4-methylpentanoyl)-3-(2-methylpropanoyl)-4-oxocyclopent-2-en-1-yl 2-methylpropyl carbonate |

TABLE 1-continued

THIAA derivatives:

| Compound name | MW | Structure | Chemical name |
|---|---|---|---|
| KDT0038 (Example 14) | 396 | 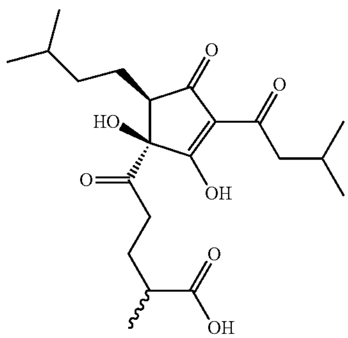 [SMILES: CC(C)CC[C@H]1C(=O)C(C(=O)CC(C)C)=C(O)[C@]1(O)C(=O)CCC(C)C(=O)O] | 5-[(1S,5R)-1,2-dihydroxy-3-(3-methylbutanoyl)-5-(3-methylbutyl)-4-oxocyclopent-2-en-1-yl]-2-methyl-5-oxopentanoic acid |
| KDT0039 | 368 | 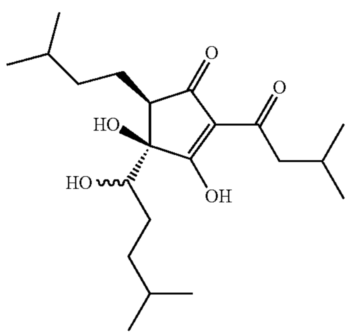 [SMILES: CC(C)CCC(O)[C@@]1(O)C(O)=C(C(=O)CC(C)C)C(=O)[C@@H]1CCC(C)C] | (4R,5R)-3,4-dihydroxy-4-(1-hydroxy-4-methylpentyl)-2-(3-methylbutanoyl)-5-(3-methylbutyl)cyclopent-2-en-1-one |
| KDT0040 (Example 15) | 378 | 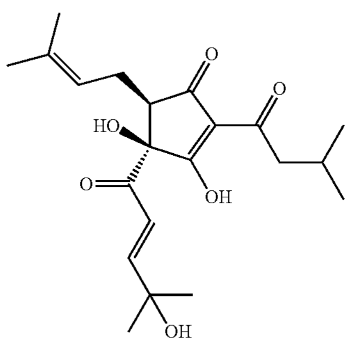 [SMILES: CC(C)=CC[C@H]1C(=O)C(C(=O)CC(C)C)=C(O)[C@]1(O)C(=O)/C=C/C(C)(C)O] | (4S,5R)-3,4-dihydroxy-4-[(2E)-4-hydroxy-4-methylpent-2-enoyl]-2-(3-methylbutanoyl)-5-(3-methylbut-2-en-1-yl)cyclopent-2-en-1-one |
| KDT0001/2 (Example 12) | 424 | 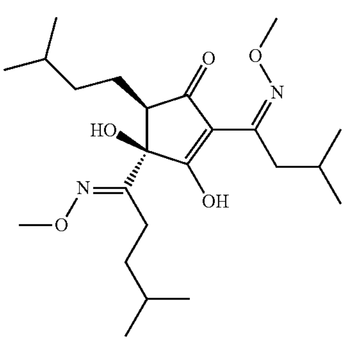 [SMILES: CO/N=C(/CC(C)C)C1=C(O)[C@](O)(/C(CCC(C)C)=N/OC)[C@@H](CCC(C)C)C1=O] | (4R,5R)-3,4-dihydroxy-2-(N-methoxy-3-methylbutanimidoyl)-4-(N-methoxy-4-methylpentanimidoyl)-5-(3-methylbutyl)cyclopent-2-en-1-one |

TABLE 1-continued

THIAA derivatives:

| Compound name | MW | Structure | Chemical name |
|---|---|---|---|
| KDT0041 (Example 6) | 449 | 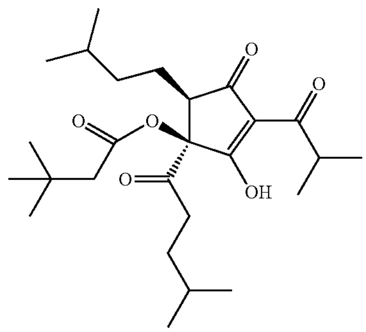 [SMILES: CC(C)CCC(=O)[C@@]1(OC(=O)CC(C)(C)C)C(O)=C(C(=O)C(C)C)C(=O)[C@@H]1CCC(C)C] | (1S,5R)-2-hydroxy-5-(3-methylbutyl)-1-(4-methylpentanoyl)-3-(2-methylpropanoyl)-4-oxocyclopent-2-en-1-yl 3,3-dimethylbutanoate |
| KDT0042 (Example 7) | 455 | 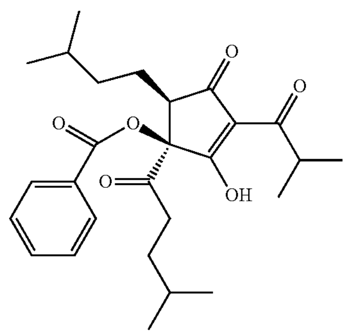 [SMILES: CC(C)CCC(=O)[C@@]1(OC(=O)c2ccccc2)C(O)=C(C(=O)C(C)C)C(=O)[C@@H]1CCC(C)C] | (1S,5R)-2-hydroxy-5-(3-methylbutyl)-1-(4-methylpentanoyl)-3-(2-methylpropanoyl)-4-oxocyclopent-2-en-1-yl benzoate |
| KDT0043 (Example 8) | 553 | 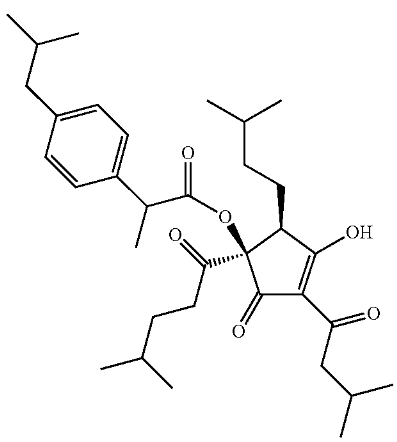 [SMILES: CC(C)CCC(=O)[C@@]1(OC(=O)C(C)c2ccc(CC(C)C)cc2)C(=O)C(C(=O)CC(C)C)=C(O)[C@@H]1CCC(C)C] | (1R,2S)-3-hydroxy-4-(3-methylbutanoyl)-2-(3-methylbutyl)-1-(4-methylpentanoyl)-5-oxocyclopent-3-en-1-yl 2-[4-(2-methylpropyl)phenyl]propanoate |
| (+)-KDT400 (Example 20) | 366 | 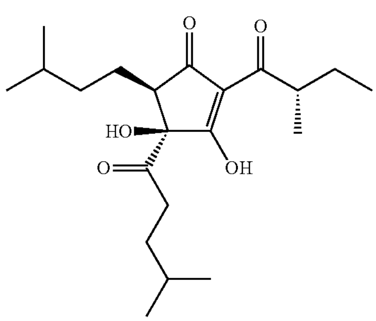 [SMILES: CC[C@H](C)C(=O)C1=C(O)[C@](O)(C(=O)CCC(C)C)[C@@H](CCC(C)C)C1=O] | (4S,5R)-3,4-dihydroxy-2-[(2S)-2-methylbutanoyl]-5-(3-methylbutyl)-4-(4-methylpentanoyl)cyclopent-2-en-1-one |

The THIAA derivatives disclosed herein were synthesized by modifying cis THIAA via acylation, enamine, oxime, and reduction protocols. cis THIAA has the structure set forth in Formula IV:

Formula IV

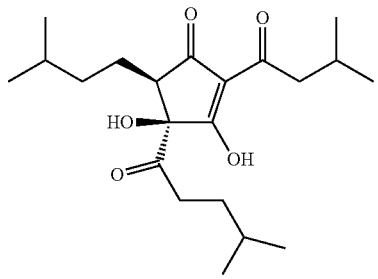

Provided herein in certain embodiments is an acylation protocol for generating THIAA derivatives having the general structure set forth in Formula V (ester) and Formula VI (carbonate), as well as compounds generated by this protocol.

Formula V

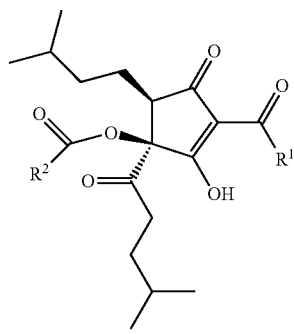

Formula VI

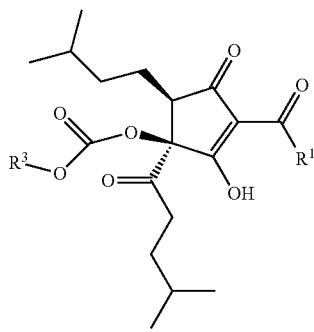

The acylation protocol provided herein comprises reacting the parent THIAA compound (tertiary alcohol with various $R^1$ groups) with acyl chlorides or anhydrides to obtain esters ($R^2$), or with alkyl chloroformates to obtain carbonates ($R^3$). This protocol allows for synthesis of THIAA derivatives with different $R^1$, $R^2$, and $R^3$ groups. In certain embodiments, $R^1$ is selected from isopropyl, isobutyl, and sec-butyl. In certain embodiments, $R^2$ is selected from any alkyl or aryl, including substituted or branched alkyls and aryls. In certain embodiments, $R^3$ is selected from any alkyl other than a tertiary alkyl.

As set forth in Examples 1-8 below, the compounds KDT0033, KDT0034, KDT0035, KDT0036, KDT0037, KDT0041, KDT0042, and KDT0043 were synthesized via an acylation protocol as provided herein. Tetrahydro isohumulone (n- or co-) was dissolved in suitable solvent (dichloromethane or chloroform), followed by addition of an excess of pyridine (5 eq.) and then an excess of acyl chloride or anhydride (3 eq.) was added. The reaction was kept at room temperature and monitored by HPLC. Once the starting material was consumed (typically 30-60 minutes for chloride, 12-24 hours for anhydrides), methanol was added to quench the excess of acyl chloride and remove a possible second acyl group from the enolized triketone. After at least an hour, the reaction mixture was evaporated and the residue was dissolved in tBuOMe, washed with 1 N HCl (2×) and brine (1×), dried over sodium sulfate, filtered, and evaporated. The residue was purified by either HPLC (C18 reverse phase, 40% acetonitrile, water, 0.05% TFA) or countercurrent chromatography (CCC) to obtain the ester (KDT0033, KDT0034, KDT0036, KDT0041, KDT0042, KDT0043). The same procedure is performed with alkyl chloroformates to obtain the carbonates (KDT0035, KDT0037).

Provided herein in certain embodiments is an enamine protocol for generating THIAA derivatives having the general structure set forth in Formula VII, as well as compounds generated by this protocol.

Formula VII

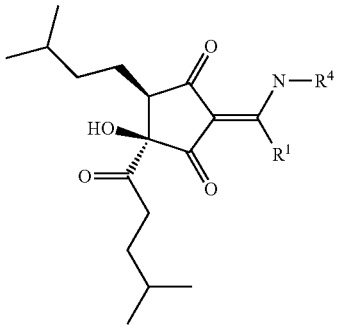

The enamine protocol provided herein comprises reacting the parent THIAA compound (tertiary alcohol with various $R^1$ groups) with primary amines. This protocol allows for synthesis of THIAA derivatives with different $R^4$ groups. In certain embodiments, $R^1$ is selected from isopropyl, isobutyl, and sec-butyl. In certain embodiments, $R^4$ is selected from any alkyl or aryl, including substituted or branched alkyls and aryls.

As set forth in Examples 9-11 below, the compounds KDT0017, KDT0020, and KDT0024 were synthesized via an enamine protocol as provided herein. Cis tetrahydro isohumulone (n- or co-) was dissolved in a suitable solvent (methanol or ethanol) and an excess of primary amine (5 eq.) was added. The reaction was kept at room temperature to 50° C. and monitored by HPLC. Once starting material was no longer present (typically 1 to 12 hours), the solvent was evaporated. In the case of volatile amines, the product could be used without further purification. In the case of non-volatile amines, the crude product was dissolved in tBuOMe, washed with 1 N HCl (2×) and brine (1×), dried over sodium sulfate, filtered, and evaporated. The residue was purified by HPLC (C18 reverse phase, 40% acetonitrile, water, 0.05% TFA).

Provided herein in certain embodiments is an oxime protocol for generating THIAA derivatives having the general structure set forth in Formulas VIII and IX, as well as compounds generated by this protocol.

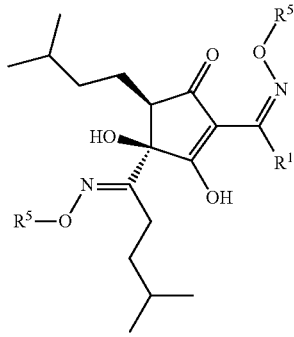

Formula VIII

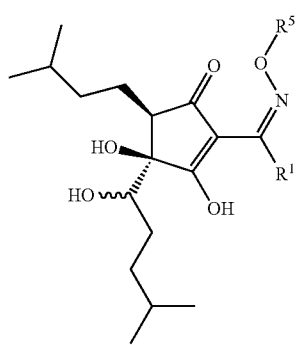

Formula IX

The oxime protocol provided herein comprises reacting the parent THIAA compound (tertiary alcohol with various $R^1$ groups) with various O-alkylated hydroxylamines. This protocol allows for synthesis of THIAA derivatives with different $R^5$ groups. In certain embodiments, R selected from isopropyl, isobutyl, and sec-butyl. In certain embodiments, $R^5$ is selected from any alkyl or aryl, including substituted or branched alkyls and aryls.

As set forth in Examples 12 and 13 below, the compounds KDT0001/2 and KDT0005 were synthesized via an oxime protocol as provided herein. Tetrahydro isohumulone (n- or co-) was dissolved in a suitable solvent (methanol or ethanol) and a slight excess of O-alkyl hydroxylamine hydrochloride was added, followed by 1 equivalent of NaOH (1 M aq. solution). The reaction was kept at room temperature and followed by HPLC. Once starting material was no longer present (typically 1 hour), the solvent was evaporated and the residue partitioned between water and tBuOMe. The organic layer was washed with 1 N HCl (2×) and brine (1×), dried over sodium sulfate, filtered, and evaporated. If necessary, this residue may be purified by HPLC (C18 reverse phase, 40% acetonitrile, water, 0.05% TFA).

Provided herein in certain embodiments is a selenium oxide protocol for generating THIAA derivatives, as well as compounds generated by this protocol. The selenium oxide protocol provided herein comprises reacting the parent THIAA compound with selenium dioxide.

As set forth in Example 15, the compound KDT0040 was synthesized via a selenium oxide protocol as provided herein. Cis isohumulone dissolved in methanol was converted to a magnesium salt, followed by addition of selenium dioxide and heating. After reaction completion, the mixture was filtered and the filtrate was evaporated, after which the residual oil was purified by simple partitioning. The aqueous phase was then evaporated to produce the final product.

As set forth in Examples 25 and 26, the THIAA derivatives set forth above were evaluated for their effect on inflammation and PPARγ activity, and certain of the derivatives were found to demonstrate anti-inflammatory and anti-diabetic properties. As shown in Example 25, certain of the derivatives were found to inhibit production of various inflammatory mediators, including $PGE_2$, NO, MMP-9, IL-1β, MCP-1, RANTES, and MIP-1α. Based on these results, methods are provided herein for inhibiting inflammation, decreased inflammatory marker levels, and treating conditions associated with inflammation such as diabetes. As shown in Example 26, certain of the derivatives were found to increase PPARγ activity, with some compounds selectively increasing PPARγ activity and others also exhibiting the ability to increase PPARα activity. Based on these results, methods are provided herein for increasing PPARγ activity either selectively or in combination with PPARα activity and for treating conditions responsive to PPARγ modulation such as type II diabetes, obesity, hyperinsulinemia, metabolic syndrome, non alcoholic fatty liver disease, non alcoholic steatohepatitis, an autoimmune disorder, or a proliferative disorder.

The term "salt" as used herein may refer to any pharmaceutically acceptable salt, including for example inorganic base salts such as potassium, aluminum, calcium, copper, guanidinium, iron, lithium, magnesium, sodium, and zinc salts and organic base salts such as cinchonidine, cinchonine, and diethanolamine salts. Additional examples of pharmaceutically acceptable salts and preparations in accordance with the present invention can be found in, for example, Berge J Pharm Sci 66:1 (1977).

Provided herein in certain embodiments are compositions comprising one or more of the THIAA derivatives provided herein. In certain of these embodiments, the compositions are substantially enantiomerically pure. The term "substantially enantiomerically pure" as used herein refers to a composition in which 90% or more of a particular compound in the composition is in a first enantiomeric form, while 10% or less is in a second enantiomeric form. In certain embodiments, the "first enantiomeric form" of a compound includes salts and crystals of that enantiomeric form. In certain embodiments, a substantially enantiomerically composition may contain 91%, 92%, 93%, 94%, 95%, 96%, 97%, 98%, 99%, 99.5%, 99.9%, 99.95%, or 99.99% or greater of a first enantiomeric form of a compound.

Provided herein in certain embodiments are pharmaceutical compositions comprising one or more of the THIAA derivatives provided herein and one or more pharmaceutically acceptable carriers. In certain embodiments, the pharmaceutical compositions are substantially enantiomerically pure. A "pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. Such a carrier may comprise, for example, a liquid or solid filler, diluent, excipient, solvent, encapsulating material, stabilizing agent, or some combination thereof. Each component of the carrier must be "pharmaceutically acceptable" in that it must be compatible with the other ingredients of the composition and must be suitable for contact with any tissue, organ, or portion of the body that it may encounter, meaning that it must not carry a risk of toxicity, irritation, allergic response, immunogenicity, or any other complication that excessively outweighs its therapeutic benefits.

Examples of pharmaceutically acceptable carriers for use in the compositions provided herein include, but are not limited to, (1) sugars, such as lactose, glucose, sucrose, or mannitol; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) disintegrating agents such as agar or calcium carbonate; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; (21) paraffin; (22) lubricants, such as talc, calcium stearate, magnesium stearate, solid polyethylene glycol, or sodium lauryl sulfate; (23) coloring agents; (24) glidants such as colloidal silicon dioxide, talc, and starch or tri-basic calcium phosphate.; and (24) other non-toxic compatible substances employed in pharmaceutical compositions such as acetone. In one embodiment, the pharmaceutically acceptable carrier used herein is an aqueous carrier, e.g., buffered saline and the like. In other embodiments, the pharmaceutically acceptable carrier is a polar solvent, e.g., acetone and alcohol.

Pharmaceutical compositions as provided herein may further comprise one or more pharmaceutically acceptable auxiliary substances as required to approximate physiological conditions. For example, compositions may comprise one or more pH adjusting agents, buffering agents, or toxicity adjusting agents, including for example sodium acetate, sodium chloride, potassium chloride, calcium chloride, sodium lactate, and the like.

Pharmaceutical compositions as provided herein may be formulated into a suitable dosage form, including for example capsules, cachets, pills, tablets, lozenges (using a flavored basis, usually sucrose and acacia or tragacanth), powders, granules, as a solution or a suspension in an aqueous or non-aqueous liquid, as an oil-in-water or water-in-oil liquid emulsion, as an elixir or syrup, or as pastilles (using an inert base, such as gelatin and glycerin, or sucrose and acacia) and/or as mouth washes and the like, each containing a predetermined amount of a THIAA derivative as an active ingredient. In certain embodiments, the compositions may be formulated as a time release delivery vehicle, such as for example a time release capsule. A "time release vehicle" as used herein refers to any delivery vehicle that releases active agent over a period of time rather than immediately upon administration. In other embodiments, the compositions may be formulated as an immediate release delivery vehicle.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a substantially enantiomerically pure mixture of the powdered THIAA derivative or further moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of a THIAA derivative therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the THIAA derivative(s) only, or preferentially, in a certain portion of the gastrointestinal tract, optionally, in a delayed manner. Examples of embedding compositions which can be used include polymeric substances and waxes. The THIAA derivative can also be in micro-encapsulated form, if appropriate, with one or more of the above-described excipients.

The concentration of THIAA derivatives in the compositions provided herein may vary. Concentrations may be selected based on fluid volumes, viscosities, body weight, and the like in accordance with the particular mode of administration selected and the biological system's needs. In certain embodiments, the concentration of a THIAA derivative in a composition provided herein may be from about 0.0001% to 100%, from about 0.001% to about 50%, from about 0.01% to about 30%, from about 0.1% to about 20%, or from about 1% to about 10% wt/vol.

In certain embodiments, the synthesis methods provided herein generate a single enantiomer of a THIAA derivative. In other embodiments, the synthesis methods result in a mixture of enantiomeric forms of THIAA derivatives. In these embodiments, one or more subsequent separation and/or purification steps may be performed to isolate a single enantiomeric form or to generate a substantially enantiomerically pure composition as provided herein.

In certain embodiments of the methods provided herein, the subject is a mammal, and in certain of these embodiments the subject is a human. A "subject in need thereof" refers to a subject diagnosed with a condition associated with inflammation or a condition responsive to PPARγ modulation, a subject who exhibits or has exhibited one or more symptoms of a condition associated with inflammation or a condition responsive to PPARγ modulation, or a subject who has been deemed at risk of developing a condition associated with inflammation or a condition responsive to PPARγ modulation based on one or more hereditary or environmental factors.

The terms "treat," "treating," or "treatment" as used herein with regards to a condition refers to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

A "therapeutically effective amount" of a THIAA derivative or pharmaceutical composition as used herein is an amount of a composition that produces a desired therapeutic effect in a subject. The precise therapeutically effective amount is an amount of the compound or composition that will yield the most effective results in terms of therapeutic efficacy in a given subject. This amount will vary depending upon a variety of factors, including but not limited to the characteristics of the therapeutic compound (including, e.g., activity, pharmacokinetics, pharmacodynamics, and bioavailability), the physiological condition of the subject (including, e.g., age, sex, disease type and stage, general physical condition, responsiveness to a given dosage, and type of medication), the nature of the pharmaceutically acceptable carrier or carriers in the composition, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005, the entire disclosure of which is incorporated by reference herein.

In certain embodiments, a compound or composition as provided herein may be administered one or more times a day. In other embodiments, the compound or composition may be delivered less than once a day. For example, the compound or composition may be administered once a week, once a month, or once every several months. Administration of a compound or composition provided herein may be carried out over a specific treatment period determined in advance, or it may be carried out indefinitely or until a specific therapeutic benchmark is reached. In certain embodiments, dosing frequency may change over the course of treatment. For example, a subject may receive less frequent administrations over the course of treatment as certain therapeutic benchmarks are met.

The compounds and compositions disclosed herein may be delivered to a subject by any administration pathway known in the art, including but not limited to oral, aerosol, enteral, nasal, ophthalmic, parenteral, or transdermal (e.g., topical cream or ointment, patch). "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Methods for preparing parenterally administrable compositions will be known or apparent to those skilled in the art and are described in more detail in such publications as Remington: The Science and Practice of Pharmacy 21st ed., Mack Publishing Company, Easton, Pa. (2005). A composition may also be administered as a bolus, electuary, or paste.

In certain embodiments, kits are provided that comprise one or more of the THIAA derivatives, pharmaceutical formulations, or substantially enantiomerically pure compositions provided herein. In certain embodiments, the kit provides instructions for usage, such as dosage or administration instructions. In certain embodiments, the kits may be used to treat a condition associated with inflammation or a condition responsive to PPARγ modulation.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1: Synthesis of (1S,5R)-2-hydroxy-5-(3-methylbutyl)-1-(4-methylpentanoyl)-3-(2-methylpropanoyl)-4-oxocyclopent-2-en-1-yl decanoate (KDT0036)

Cis tetrahydro isocohumulone (38 mg) was dissolved in chloroform (1 mL) and pyridine was added (75 μL, 11 eq.), followed immediately by acetic anhydride (120 μL, 9 eq). The mixture was kept at room temperature overnight, quenched with MeOH (1 mL), and left overnight again. The reaction mixture was then evaporated, and the residue was dissolved in tBuOMe, washed with 1 N HCl (2×) and brine (1×), dried over sodium sulfate, filtered, and evaporated to an oil. The crude product was purified by HPLC. Pure fractions were combined and evaporated to give a pure product as a colorless oil (11.6 mg, ~21% yield). MS 505.5 [M-H]$^-$, UV$_{max}$ (aq. MeOH, 50 mM ammonium acetate buffer, pH=9.5) 259 nm.

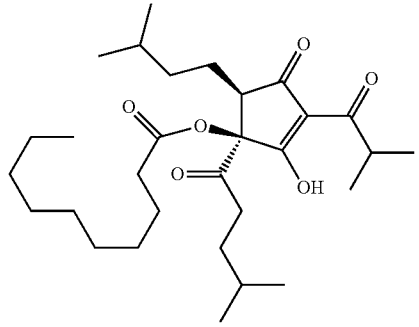 [SMILES: CCCCCCCCCC(=O)O[C@]1(C(=O)CCC(C)C)C(O)=C(C(=O)C(C)C)C(=O)[C@@H]1CCC(C)C]

Example 2: Synthesis of (1S,5R)-2-hydroxy-3-(3-methylbutanoyl)-5-(3-methlbutyl)-1-(4-methylpentanoyl)-4-oxocyclopent-2-en-1-yl 3,3-dimethylbutanoate (KDT0034)

Cis tetrahydro isohumulone (51 mg) was dissolved in chloroform (1 mL) and pyridine was added (60 μL, 5.3 eq), followed immediately by dimethylpropionlyl chloride (60 μL, 3.1 eq). The mixture was kept at room temperature for 3 hours, quenched with MeOH (1 mL), and left standing at room temperature overnight. The reaction mixture was then evaporated, and the residue was dissolved in tBuOMe, washed with 1 N HCl (2×) and brine (1×), dried over sodium sulfate, filtered, and evaporated to obtain 58 mg of an oil. The crude product was purified by HPLC. Pure fractions were combined and evaporated to give a pure product as a colorless oil (22.0 mg, ~34% yield). MS 463.7 [M-H]$^-$, UV$_{max}$ (aq. MeOH, 50 mM ammonium acetate buffer, pH=9.5) 259 nm.

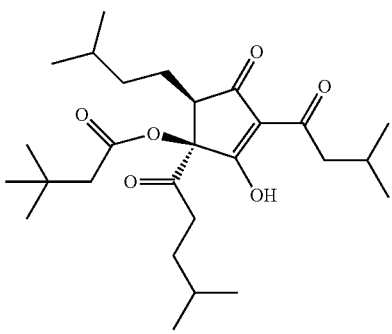 [SMILES: CC(C)CCC(=O)[C@@]1(OC(=O)CC(C)(C)C)C(O)=C(C(=O)CC(C)C)C(=O)[C@@H]1CCC(C)C]

Example 3: Synthesis of (1S,5R)-2-hydroxy-3-(3-methylbutanoyl)-5-(3-methylbutyl)-1-(4-methylpentanoyl)-4-oxocyclopent-2-en-1-yl 2,2-dimethylpropanoate (KDT0033)

Cis tetrahydro isohumulone (51.5 mg) was dissolved in chloroform (1 mL) and pyridine was added (60 μL, 5.3 eq) followed immediately by pivaloyl chloride (60 μL, 3.5 eq). The mixture was kept at room temperature for 90 minutes, quenched with MeOH (1 mL), and left standing at room temperature overnight. The reaction mixture was then evaporated, and the residue was dissolved in tBuOMe, washed with 1 N HCl (2×) and brine (1×), dried over sodium sulfate, filtered, and evaporated to obtain 58 mg of an oil. The crude product was purified by HPLC. Pure fractions were combined and evaporated to give pure product as a colorless oil (23.0 mg, ~36% yield). MS 449.5 [M-H]⁻, $UV_{max}$ (aq. MeOH, 50 mM ammonium acetate buffer, pH=9.5) 259 nm.

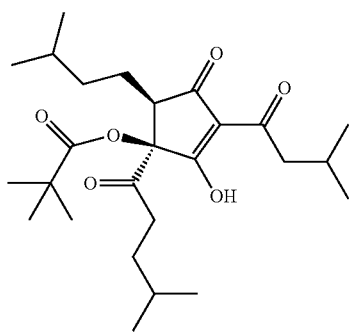 [SMILES: CC(C)CCC(=O)[C@@]1(OC(=O)C(C)(C)C)C(O)=C(C(=O)CC(C)C)C(=O)[C@@H]1CCC(C)C]

Example 4: Synthesis of but-3-yn-1-yl (1S,5R)-2-hydroxy-3-(3-methylbutanoyl)-5-(3-methylbutyl)-1-(4-methylpentanoyl)-4-oxocyclopent-2-en-1-yl carbonate (KDT0035)

Cis tetrahydro isohumulone (60.4 mg) was dissolved in chloroform (1 mL) and pyridine was added (50 μL, 3.7 eq) followed by butinyl chloroformate (55 μL, 2.9 eq). The mixture was kept at room temperature for 3 hours, quenched with MeOH (1 mL), and left standing at room temperature for 1 hour. The reaction mixture was then evaporated, and the crude product was purified by HPLC. Pure fractions were combined and evaporated to give pure product as a colorless oil (29.7 mg, ~39% yield). MS 461 [M-H]⁻, $UV_{max}$ (aq. MeOH, 50 mM ammonium acetate buffer, pH=9.5) 259 nm.

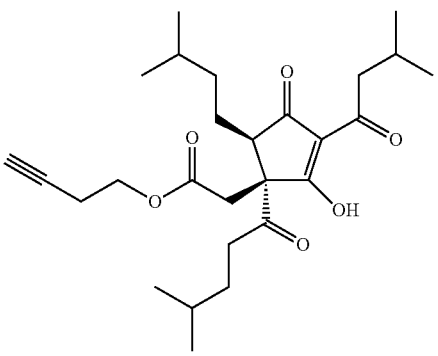 [SMILES: C#CCCOC(=O)C[C@]1(C(=O)CCC(C)C)C(O)=C(C(=O)CC(C)C)C(=O)[C@@H]1CCC(C)C]

Example 5: Synthesis of (1S,5R)-2-hydroxy-5-(3-methylbutyl)-1-(4-methylpentanoyl)-3-(2-methylpropanoyl)-4-oxocyclopent-2-en-1-yl 2-methylpropyl carbonate (KDT0037)

Cis tetrahydro isocohumulone (55.2 mg) was dissolved in dichloromethane (1 mL) and pyridine was added (50 μL, 4.0 eq) followed by isobutyl chloroformate (60 μL, 2.9 eq). The mixture was kept at room temperature for 1 hour, quenched with MeOH (1 mL), and left standing at room temperature for 1 hour. The reaction mixture was then evaporated, and the crude product was purified by HPLC. Pure fractions were combined and evaporated to give pure product as a colorless oil (10.3 mg, ~15% yield). MS 451 [M-H]⁻, $UV_{max}$ (aq. MeOH, 50 mM ammonium acetate buffer, pH=9.5) 259 nm.

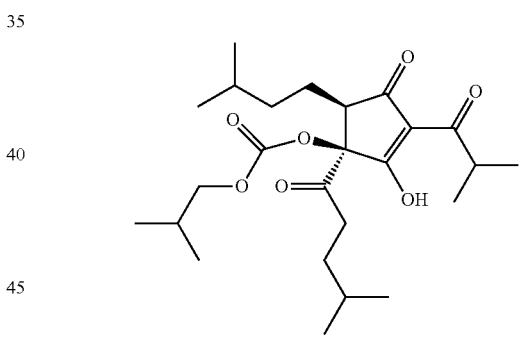

Example 6: Synthesis of (1S,5R)-2-hydroxy-5-(3-methylbutyl)-1-(4-methylpentanoyl)-3-(2-methylpropanoyl)-4-oxocyclopent-2-en-1-yl 3,3-dimethylbutanoate (KDT0041)

Cis tetrahydro isocohumulone (55.1 mg) was dissolved in chloroform (1 mL) and pyridine was added (60 μL, 4.8 eq) followed immediately by dimethylpropionlyl chloride (60 μL, 2.8 eq). The mixture was kept at room temperature for 1 hour, quenched with MeOH (1 mL), and left standing at room temperature overnight. The reaction mixture was then evaporated to an oil and the crude product was purified by HPLC. Pure fractions were combined and evaporated to give pure product as a colorless oil (30.5 mg, ~43% yield). MS 449.4 [M-H]⁻, $UV_{max}$ (aq. MeOH, 50 mM ammonium acetate buffer, pH=9.5) 258 nm, ¹H NMR (600 MHz, METHANOL-$d_4$) δ ppm 0.82-0.90 (dd, 12H) 1.05 (s, 3H) 1.10 (s, 9H) 1.12 (s, 3H) 1.26-1.44 (m, 5H) 1.44-1.50 (m, 4H) 2.57 (dt, J=18.41, 7.33 Hz, 1H) 2.82 (dt, J=7.50, 18.08 Hz, 1H) 3.54 (t, J=6.62 Hz, 1H).

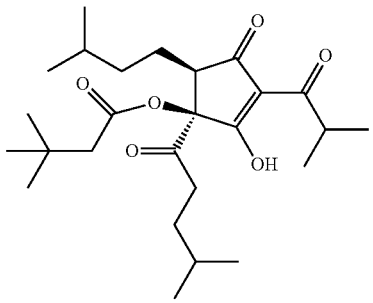 [SMILES: CC(C)CCC(=O)[C@@]1(OC(=O)CC(C)(C)C)C(O)=C(C(=O)C(C)C)C(=O)[C@@H]1CCC(C)C]

Example 7: Synthesis of (1S,5R)-2-hydroxy-5-(3-methylbutyl)-1-(4-methylpentanoyl)-3-(2-methylpropanoyl)-4-oxocyclopent-2-en-1-yl benzoate (KDT0042)

Cis tetrahydro isocohumulone (56.2 mg) was dissolved in chloroform (1 mL) and pyridine was added (60 μL, 4.7 eq) followed immediately by benzoyl chloride (30 μL, 1.6 eq). The mixture was kept at room temperature for 1 hour, quenched with MeOH (1 mL), and left standing at room temperature overnight. The reaction mixture was then evaporated to an oil and the crude product was purified by HPLC. Pure fractions were combined and evaporated to give pure product as a colorless oil (14.9 mg, ~20% yield). MS 455.4 [M-H]$^-$, UV$_{max}$ (aq. MeOH, 50 mM ammonium acetate buffer, pH=9.5) 234 nm, $^1$H NMR (600 MHz, METHANOL-d$_4$) δ ppm 0.62 (dd, J=9.26, 6.62 Hz, 6H) 0.74-0.78 (m, 6H) 1.02 (d, J=7.06 Hz, 3H) 1.08-1.12 (m, 3H) 1.13-1.30 (m, 3H) 1.30-1.42 (m, 3H) 1.43-1.58 (m, 2H) 2.47-2.56 (m, 1H) 2.79 (ddd, J=18.08, 8.16, 6.39 Hz, 1H) 3.43 (dt, J=13.67, 6.84 Hz, 1H) 3.64 (t, J=6.17 Hz, 1H) 7.46-7.55 (m, 2H) 7.62-7.68 (m, 1H) 8.01-8.11 (m, 2H).

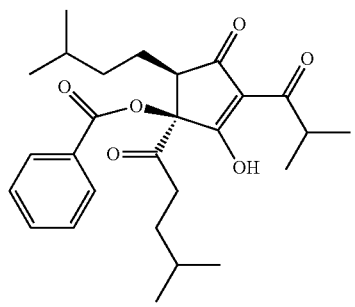 [SMILES: CC(C)CCC(=O)[C@@]1(OC(=O)c2ccccc2)C(O)=C(C(=O)C(C)C)C(=O)[C@@H]1CCC(C)C]

Example 8: Synthesis of (1R,2S)-3-hydroxy-4-(3-methylbutanoyl)-2-(3-methylbutyl)-1-(4-methylpentanoyl)-5-oxocyclopent-3-en-1-yl 2-[4-(2-methylpropyl)phenyl]propanoate (KDT0043)

Cis tetrahydro isohumulone (52 mg) was dissolved in dichloromethane (2 mL) and ibuprofen chloride (69 mg, 2.2 eq) was added, followed immediately by pyridine (60 μL, 5 eq.). The mixture was kept at room temperature for 3 hours, quenched with MeOH (1 mL), and left overnight. The reaction mixture was then evaporated, and the residue was dissolved in tBuOMe, washed with 1 N HCl (2×) and brine (1×), dried over sodium sulfate, filtered, and evaporated to obtain 124 mg of oil. This crude product was purified by CCC in Hexane/DMF in descending mode. Pure fractions were combined and evaporated to obtain pure product as a colorless oil (30 mg, ~38% yield). MS 553.4 [M-H].

In an alternative procedure, cis tetrahydro isohumulone (52 mg) was dissolved in dichloromethane (2 ml) and ibuprofen chloride (36 mg, 1.1 eq.) was added, followed immediately by pyridine (30 μL, 2.6 eq.). The mixture was kept at room temperature for 75 minutes, quenched with water (100 μL), and stirred for 1 hour. The reaction mixture was then evaporated, and the residue was dissolved in tBuOMe and washed with water (1×), sat. aq. sodium bicarbonate (1×), 1 N HCl (3×), and brine (1×), dried over sodium sulfate, filtered, and evaporated to obtain 73.1 mg (93% yield) of the product.

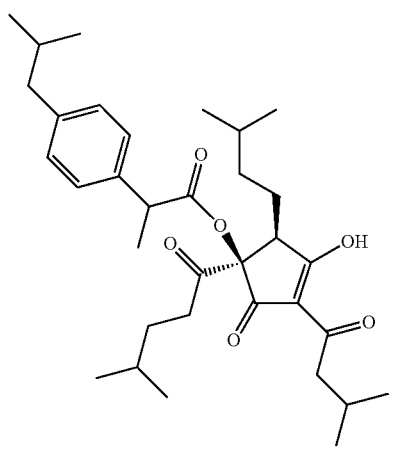 [SMILES: CC(C)CCC(=O)[C@@]1(OC(=O)C(C)c2ccc(CC(C)C)cc2)C(=O)C(C(=O)CC(C)C)=C(O)[C@@H]1CCC(C)C]

Example 9: Synthesis of (4R,5R)-4-hydroxy-5-(3-methylbutyl)-2-[3-methyl-1-(methylamino)butylidene]-4-(4-methylpentanoyl)cyclopentane-1,3-dione (KDT0020)

Cis tetrahydro isohumulone (8.1 mg) was dissolved in methanol (100 μL) and methylamine (50 μL, 33% solution in ethanol, 18 eq) was added. The mixture was kept at room temperature for 1 hour and evaporated to obtain a white solid (8.0 mg, ~95% yield). MS 378.3 [M-H]$^-$, UV$_{max}$ (aq. MeOH, 50 mM ammonium acetate buffer, pH=9.5) 248, 303 nm.

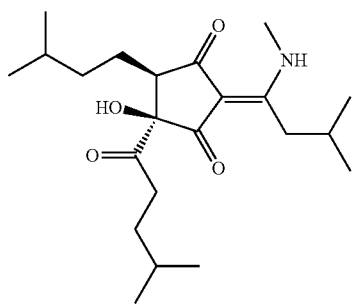 [SMILES: CN/C(CC(C)C)=C1\C(=O)[C@H](CCC(C)C)[C@@](O)(C(=O)CCC(C)C)C1=O]

Example 10: Synthesis of (4R,5R)-4-hydroxy-2-{1-[(2-hydroxyethyl)amino]-3-methylbutylidene}-5-(3-methylbutyl)-4-(4-methylpentanoyl)cyclopentane-1,3-dione (KDT0017)

Cis tetrahydro isohumulone (48.0 mg) was dissolved in methanol (200 μL) and ethanolamine (100 μL, 12.7 eq.) was added. The mixture was stirred at 40° C. for 15 hours, evaporated, and purified by HPLC to obtain a white solid (31.3 mg, ~58% yield). MS 408.5 [M-H]⁻, $UV_{max}$ (aq. MeOH, 50 mM ammonium acetate buffer, pH=9.5) 247, 303 nm.

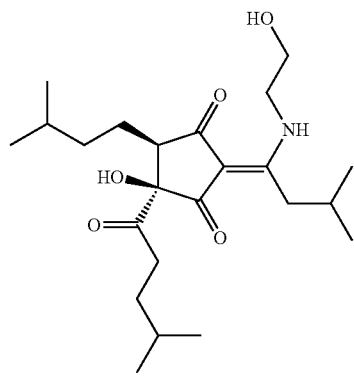 [SMILES: CC(C)CCC(=O)[C@@]1(O)C(=O)/C(=C(\CC(C)C)NCCO)C(=O)[C@@H]1CCC(C)C]

Example 11: Synthesis of (4R,5R)-2-[1-(benzylamino)-3-methylbutylidene]-4-hydroxy-5-(3-methylbutyl)-4-(4-methylpentanoyl)cyclopentane-1,3-dione (KDT0024)

Cis tetrahydro isohumulone (25.9 mg) was dissolved in methanol (75 μL) and benzylamine (35 μL, 4.5 eq.) was added. The mixture was stirred at room temperature for 2 hours, evaporated, and purified by HPLC to give a white solid (20.3 mg, ~63% yield). MS 454.5 [M-H]⁻, $UV_{max}$ (aq. MeOH, 50 mM ammonium acetate buffer, pH=9.5) 247, 307 nm.

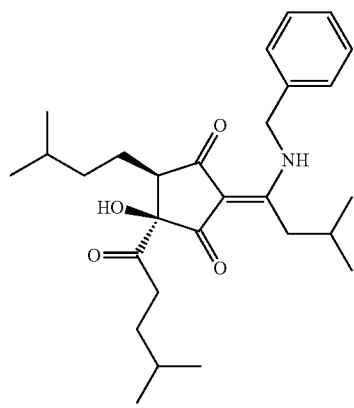 [SMILES: CC(C)CCC(=O)[C@@]1(O)C(=O)/C(=C(\CC(C)C)NCc2ccccc2)C(=O)[C@@H]1CCC(C)C]

Example 12: Synthesis of (4R,5R)-3,4-dihydroxy-24N-methoxy-3-methylbutanimidoyl)-4-(N-methoxy-4-methylpentanimidoyl)-5-(3-methylbutyl)cyclopent-2-en-1-one (KDT0001/2)

Cis tetrahydro isohumulone potassium salt (96.8 mg) was dissolved in methanol (3 mL) and O-Me-hydroxylamine. HCl (50.5 mg, 2.3 eq) was added, followed by NaOH (280 μL of 1 M aq. solution, 1.06 eq). The mixture was kept at room temperature for 16 hours, the methanol was evaporated, and the residue partitioned between water and tBuOMe. The organic layer was washed with 1 N HCl (2×) and brine (1×), dried over sodium sulfate, filtered, and evaporated to obtain a white solid (107.2 mg, ~96% yield). MS 423.5 [M-H]⁻, $UV_{max}$ (aq. MeOH, 50 mM ammonium acetate buffer, pH=9.5) 271 nm.

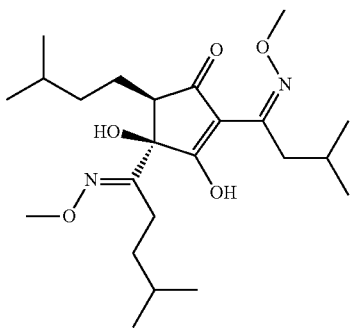 [SMILES: CO/N=C(/CC(C)C)C1=C(O)[C@](O)(/C(CCC(C)C)=N/OC)[C@@H](CCC(C)C)C1=O]

Example 13: Synthesis of (4R,5R)-3,4-dihydroxy-4-(1-hydroxy-4-methylpentyl)-2-(N-methoxy-3-methylbutanimidoyl)-5-(3-methylbutyl)cyclopent-2-en-1-one (KDT0005)

Cis hexahydro isohumulone (23.0 mg) was dissolved in methanol (2 mL) and O-Me-hydroxylamine. HCl (11 mg, 2.1 eq) was added followed by NaOH (80 μL of 1 M aq. solution, 1.3 eq.). The mixture was kept at room temperature for 2 hours, the methanol was evaporated, and the residue was partitioned between water and tBuOMe. The organic layer was washed with 1 N HCl (2×) and brine (1×), dried over sodium sulfate, filtered, and evaporated to obtain a white solid (21.2 mg, ~85% yield). MS 396.1 [M-H]⁻, $UV_{max}$ (aq. MeOH, 50 mM ammonium acetate buffer, pH=9.5) 269 nm.

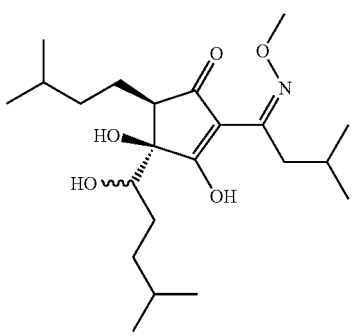 [SMILES: CO/N=C(/CC(C)C)C1=C(O)[C@](O)(C(O)CCC(C)C)[C@@H](CCC(C)C)C1=O]

Example 14: 5-[(1S,5R)-1,2-dihydroxy-3-(3-methylbutanoyl)-5-(3-methylbutyl)-4-oxocyclopent-2-en-1-yl]-2-methyl-5-oxopentanoic acid (KDT0038)

Urine (750 mL) from a patient dosed with 1.2 g of THIAA/day (½ of 24 hour collection) was acidified with 50 mL of 1 N HCl, mixed with dichloromethane (100 mL), and the precipitate removed by filtration. The residue was partitioned and the aqueous layer was extracted 2 additional times with 100 mL of dichloromethane. The combined dichloromethane extracts were filtered through celite and the filtrate was washed with brine (1×100 mL), dried over sodium sulfate, filtered and evaporated to obtain 168 mg of a yellow oil. The oil was purified by semi-preparative HPLC (100 mM ammonium acetate pH 9.5, 40% MeOH, 4.6×250 GeminiNX column) to obtain a white solid. MS 395.4 [M-H]$^-$, UV$_{max}$ (aq. MeOH, 50 mM ammonium acetate buffer, pH 9.5) 255 nm. $^1$H NMR (500 MHz, METHANOL-d$_4$) δ ppm 0.86-0.94 (m, 4H) 0.94-1.04 (m, 6H) 1.09-1.15 (m, 1H) 1.15-1.23 (m, 3H) 1.24-1.36 (m, 3H) 1.48-1.60 (m, 1H) 1.60-1.78 (m, 3H) 1.80-1.92 (m, 1H) 2.08-2.21 (m, 1H) 2.43 (dq, J=14.12, 7.21 Hz, 1H) 2.68-2.81 (m, 2H) 2.81-2.90 (m, 2H) 3.08 (t, J=6.51 Hz, 1H).

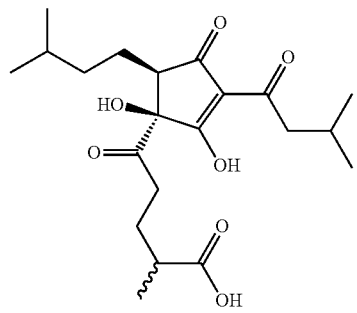 [SMILES: CC(C)CC[C@H]1C(=O)C(C(=O)CC(C)C)=C(O)[C@]1(O)C(=O)CCC(C)C(=O)O]

Example 15: (4S,5R)-3,4-dihydroxy-4-[(2E)-4-hydroxy-4-methylpent-2-enoyl]-2-(3-methylbutanoyl)-5-(3-methylbut-2-en-1-yl)cyclopent-2-en-1-one (KDT0040)

Magnesium oxide (11 mg, 1.1 eq.) was added to cis isohumulone (95.0 mg) in methanol and mixed briefly to form the salt. Selenium dioxide (76 mg, 2.9 eq.) was then added and the reaction mixture was heated at 65° C. for 80 minutes, at which point the reaction had reached completion. The reaction mixture was filtered through celite and the filtrate was evaporated. The residual oil was purified by simple partitioning in HEMW at 1111 (Hexane-Ethyl acetate-Methanol-Water, 1:1:1:1 by volume), with the product in aqueous phase and the remaining starting material and impurities in the organic phase. The aqueous phase was evaporated to obtain a white solid. MS 377.1 [M-H]$^-$, UV$_{max}$ (aq. MeOH, 50 mM ammonium acetate buffer, pH=9.5) 245 nm. $^1$H NMR (500 MHz, METHANOL-d$_4$) δ ppm 0.98 (m, 6H) 1.35 (s, 6H) 1.62 (s, 3H) 1.66 (s, 3H) 2.15 (m, 1H) 2.35-2.57 (m, 2H) 2.66-2.84 (m, 2H) 3.19 (t, J=5.7, 1H) 3.89 (s, 1H) 5.14 (t, J=6.7 Hz, 1H) 6.89 (d, J=15.6 Hz, 11-1H) 7.05 (d, J=15.6 Hz, 1H).

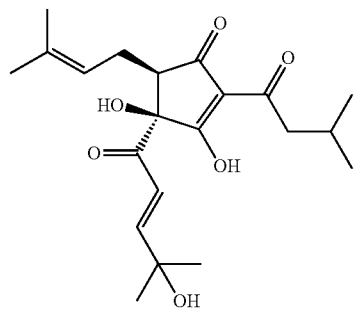 [SMILES: CC(C)=CC[C@H]1C(=O)C(C(=O)CC(C)C)=C(O)[C@]1(O)C(=O)/C=C/C(C)(C)O]

Example 16: (4S,5R)-3,4-dihydroxy-5-(3-methylbutyl)-4-(4-methylpentanoyl)-2-(2-methylpropanoyl) cyclopent-2-en-1-one ((+)-KDT100; (+)-cis tetrahydro isocohumulone)

The trans iso-α-acids were removed via β-cyclodextrin complexation (Khatib 2010) from 45 g of a hops isomerized resin extract. The cis material was further purified via CCC (Dahlberg 2012) in order to isolate cis isocohumulone. Cis isocohumulone was reduced via catalytic hydrogenation and repurified via CCC (Dahlberg 2010) to ≥95% homogeneity.

Anal. Found: C, 68.09; H, 9.11. $C_{20}H_{32}O_5$ requires C, 68.15; H, 9.15. m.p. 49-50° C. (50-52° C.), optical rotation +35.3, c=1.0, MeOH (35.6) (Ting 1996).

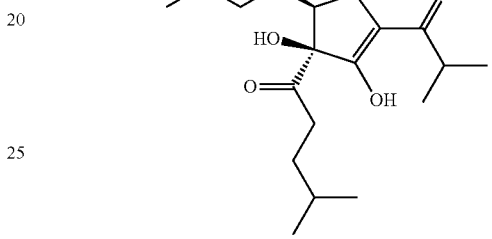

Example 17: Cinchonidine Salt of (+)-KDT100

One equivalent each of (+)-KDT100 (77.0 mg) and (-)-cinchonidine (51.9 mg, 1.00 eq.) were mixed in $^i$Pr—OH (200 μL) and briefly heated to form a solution. $^t$BuOMe (200 μL) was added and the resulting solution was left to crystallize at room temperature. After three days, the in situ formation of crystals was observed in this solution. An individual crystal suitable for X-ray analysis was identified, carefully removed, mounted and submitted for X-ray diffraction analysis.

Anal. (Calc 2M+$^t$BuOMe, formula corresponding to crystal structure). Found: C, 72.14; H, 8.42; N, 4.09. $C_{83}H_{120}N_4O_{13}$ requires C, 71.90; H, 8.75; N, 4.05. m.p. 118° C.

Example 18: (4S,5S)-3,4-dihydroxy-2-(3-methylbutanoyl)-5-(3-methylbutyl)-4-(4-methylpentanoyl) cyclopent-2-en-1-one ((+)-KDT700; (-)-trans tetrahydro isohumulone)

The alpha acids were isolated from a commercially available hops $CO_2$ extract via a differential pH extraction. A 450 mm jacketed borosilicate glass immersion well was wrapped with approximately 17 meters of 2.7 mm inner diameter FEP tubing and was used with a 450 W medium pressure mercury immersion lamp to produce a flow photoreactor. The isolated alpha acids (2.1 g) were dissolved in 100 mL of methanol and run through the flow reactor at 5 mL/min for two hours, recycling the effluent until the reaction was complete. The resulting free acid mixture of trans iso-alpha-acids was reduced via catalytic hydrogenation and purified via CCC to produce trans tetrahydro isohumulone (Dahlberg 2010) in ≥95% homogeneity.

Anal. Found: C, 68.05; H, 9.56; N, 5.77. $C_{27}H_{44}N_2O_5$ requires C, 68.04; H, 9.30; N, 5.88. m.p. 76° C. (78-81° C.) (Ting 1996), optical rotation -11.2, c=1.0, MeOH (-12.4)

(Ting 1996). $^1$H NMR (500 MHz, METHANOL-$d_4$) δ ppm 0.88-0.95 (m, 12H) 0.98 (dd, J=16.30, 6.68, Hz, 6H) 1.18-1.26 (m, 1H) 1.37-1.49 (m, 4H) 1.50-1.60 (m, 2H) 1.87-1.97 (m, 1H) 2.09-2.19 (m, 1H) 2.68-2.75 (m, 1H) 2.75-2.86 (m, 4H); $^{13}$C NMR (126 MHz, METHANOL-$d_4$) δ ppm 21.26, 21.31, 21.36, 21.37, 21.49, 21.58, 22.19, 26.28, 27.25, 27.93, 31.35, 36.70, 37.04, 44.14, 47.10, 47.27, 47.44, 47.61, 47.79, 47.95, 48.12, 191.45, 196.44, 207.67, 210.23.

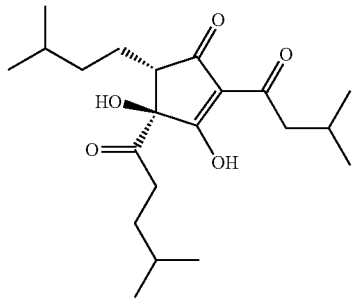 [SMILES: CC(C)CCC(=O)[C@@]1(O)C(O)=C(C(=O)CC(C)C)C(=O)[C@H]1CCC(C)C]

Example 19: Cinchonidine Salt of (−)-KDT700

(−)-KDT700 (54.3 mg) was mixed with cinchonine (43.0 mg, 1 eq) in MeOH and the resulting solution was evaporated. The resulting solid salt was suspended in hexane and chloroform was added until complete dissolution occurred. The solution was left open to allow the solvent to slowly evaporate over several days, at which time crystals formed. An individual crystal suitable for X-ray analysis was identified, carefully removed, mounted and submitted to X-ray diffraction analysis. The remaining crystals were filtered, dried at high vacuum and submitted for elemental analysis.

Anal. (Calc. as M+0.15CHCl$_3$). Found: C71.26; H, 8.35; N, 4.15. $C_{40.15}H_{56.1}Cl_{0.45}N_2O_6$ requires C, 71.04, 8.34; N, 4.13. m.p. 137-139° C.

Example 20: (4S,5R)-3,4-dihdroxy-2-[(2S)-2-methylbutanoyl]-5-(3-methylbutyl)-4-(4-methylpentanoyl)cyclopent-2-en-1-one ((+)-KDT400; (+)-cis tetrahydro isoadhumulone)

The trans iso-α-acids were removed via β-cyclodextrin complexation (Khatib 2010) from 45 g of a hops isomerized resin extract. The cis material was further purified via CCC (Dahlberg 2012) in order to isolate cis isoadhumulone, which was then reduced via catalytic hydrogenation and repurified via CCC (Dahlberg 2010) to ≥95% homogeneity.

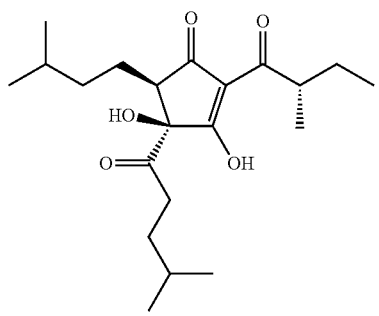 [SMILES: CC[C@H](C)C(=O)C1=C(O)[C@](O)(C(=O)CCC(C)C)[C@@H](CCC(C)C)C1=O]

Example 21: Cinchonidine Salt of (+)-KDT400

One equivalent each of (+)-KDT400 (50.0 mg) and (−)-cinchonidine (39.9 mg, 0.99 eq.) were mixed in $^i$Pr—OH (200 μL) in a 4 mL amber-colored vial and briefly heated at 60-70° C. to form a solution. Ether (200 μL) was added and the resulting solution was left to form crystals at room temperature. The solution was sealed under a septum, which was then pierced with a Gauge 16 needle to enable gradual evaporation of solvent. After three days at room temperature, the in situ formation of crystals was observed in this solution. An individual crystal suitable for X-ray analysis was identified, carefully removed, mounted and submitted for X-ray diffraction analysis.

Anal. (Calc as 2M+0.6 iPrOH+0.4 Et2O, formula corresponding to crystal structure). Found: C, 70.68; H, 8.35; N, 3.98. $C_{83.4}H_{120.8}N_4O_{13}$ requires C70.57; H, 8.58; N, 3.95. m.p. 149° C.

Example 22: (4S,5R)-3,4-dihydroxy-2-(3-methylbutanoyl)-5-(3-methylbut-2-en-1-yl)-4-(4-methylpent-3-enoyl)cyclopent-2-en-1-one ((+)-KDT550; (+)-cis isohumulone)

The trans iso-alpha acids were removed via β-cyclodextrin complexation (Khatib 2010) from 45 g of a hops isomerized resin extract. The cis material was further purified via CCC (Dahlberg 2012) in order to isolate cis isohumulone, which was confirmed to ≥95% homogenous following purification.

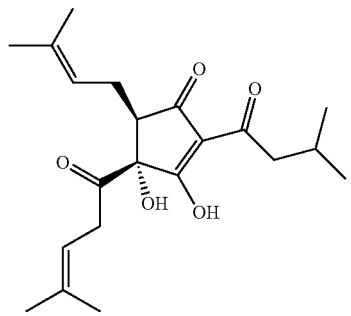 [SMILES: CC(C)=CCC(=O)[C@]1(O)C(O)=C(C(=O)CC(C)C)C(=O)[C@@H]1CC=C(C)C]

Example 23: Cinchonidine Salt of (+)-KDT500

One equivalent each of (+)-KDT500 (99.4 mg) and (−)-cinchonidine (80.0 mg, 0.99 eq.) were mixed in $^i$Pr—OH (100 μL) and briefly heated to form a solution. $^t$BuOMe (500 μL) was added and the resulting solution was left to form crystals at room temperature. After three days the in situ formation of crystals was observed in this solution. An individual crystal suitable for X-ray analysis was identified, carefully removed, mounted and submitted for X-ray diffraction analysis.

Anal. (Calc as M+0.3 H$_2$O). Found: C, 72.65; H, 7.80; N, 4.28. $C_{40}H_{52.6}O_{6.3}$ requires C, 72.53; H, 8.02; N, 4.23. m.p. 149° C.

Example 24: (6S)-3,5,6-trihydroxy-2-(3-methylbutanoyl)-4,6-bis(3-methylbut-2-en-1-yl)cyclohexa-2,4-dien-1-one ((+)-KDT505; (−) humulone)

(−) humulone was isolated from a commercially available hops CO$_2$ extract via a differential pH extraction, followed by CCC purification of the resultant alpha acid fraction to 95% homogeneity. m.p. 66° C. (66° C. (Ting 1996)), optical rotation −197.7, c=1.0, MeOH (−212 (Ting 1996)). 1,2-Diamincyclohexane salt: Anal. Found: C, 68.05; H, 9.56; N, 5.77. $C_{27}H_{44}N_2O_5$ requires C, 68.05; H, 9.30; N, 5.88. m.p. 144° C.

Example 25: Effect of THIAA Derivatives on LPS-mediated Production of Inflammatory Mediators THIAA derivatives synthesized in Examples 1-19 were dissolved in dimethyl sufoxide (DMSO) and stored at −20° C. LPS was purchased from Sigma Chemicals (St. Louis, Mo.).

The effect of the THIAA derivatives on LPS-mediated prostaglandin E2 ($PGE_2$) and nitric oxide (NO) production was evaluated in a RAW264.7 murine macrophage model. The RAW 264.7 cell line was purchased from ATCC (Manassas, Va.) and maintained according to their instructions. Cells were grown and subcultured in 96-well plates at a density of $8 \times 10^4$ cells per well, and reached 80-90% confluence the next day. THIAA derivatives were added to the cells in serum-free medium at a final concentration of 0.1% DMSO. Following one hour of incubation with the THIAA derivatives, LPS (1 μg/ml) or DMEM medium alone was added to the cells and incubation was continued for 6 hours. Stimulation of RAW 264.7 cells with LPS (1 μg/ml) for 6 hours activated the production of $PGE_2$ and NO. Supernatant media was collected for measurement of $PGE_2$ levels. For NO, incubations were continued overnight. Supernatant media was collected for measurement of NO levels after 16 hours of stimulation. $PGE_2$ levels were measured using assay kits from Assay Designs, (Ann Arbor, Mich.) and NO levels were measured using assay kits from Cayman Chemicals (Ann Harbor, Mich.).

The effect of the THIAA derivatives on LPS-mediated MMP-9, IL-1β, MCP-1, RANTES, and MIP-1α was evaluated in THP-1 cells. Stimulation of THP-1 cells with LPS (1 μg/ml) activated the production of MMP-9, IL-1β, MCP-1, RANTES, and MIP-1α.

Results are summarized in Table 2, with data represented as % inhibition of inflammatory mediator production.

In RAW264.7 cells, many of the test compounds inhibited LPS-mediated $PGE_2$ and NO production to a significant degree (defined as greater than 20%). The efficacy of inhibition varied between test compounds. For example, KDT0033, KDT0034, and KDT0037 inhibited both $PGE_2$ and NO production by more than 50%, while KDT100, KDT700, KDT0005, KDT0017, KDT0038, and KDT0039 showed weak (<20%) or no inhibition of both inflammatory mediators. Rosiglitazone, a positive control agonist for PPARγ, did not inhibit $PGE_2$ production and inhibited NO production very weakly (6%), suggesting that the anti-inflammatory effects of THIAA derivatives are independent of PPARγ activation in the RAW2564.7 cell model.

In THP-1 cells, all of the KDT test compounds inhibited LPS-induced expression of one or more of MMP-9, IL-1β, MCP-1, RANTES, and MIP-1α at a concentration of 12.5 μM. Again, rosiglitazone showed no inhibition or only weak inhibition of inflammatory mediator production, suggesting that the anti-inflammatory effects of the KDT test molecules are independent of PPARγ activation in the THP-1 cell model.

Mean inhibition across all six inflammatory mediators was calculated for each of the THIAA derivatives. Many of the test compounds exhibited significant mean inhibition levels, with KDT0033 and KDT0034 exhibiting mean inhibition levels of nearly 90%. Interestingly, THIAA derivatives functionalized at the $R^2$ (i.e., KDT0033, KDT0034, KDT0035, KDT0036, and KDT0037) position appear to have enhanced anti-inflammatory effects in both cell models.

Example 26: Effect of THIAA Derivatives on PPARα and PPARγ Activity

The functional effect of THIAA derivatives on PPARα and PPARγ activity was evaluated using a PPAR reporter assay (INDIGO Biosciences, Pa.). This assay utilizes non-human mammalian cells engineered to provide constitutive

TABLE 2

Effect of THIAA derivatives on LPS-mediated inflammatory mediators in RAW264.7 and THP-1 cells:

| Test compound (12.5 μM) | RAW264.7 cells | | THP-1 cells | | | | |
|---|---|---|---|---|---|---|---|
| | % inhibition of $PGE_2$ production | % inhibition of NO production | % inhibition of IL-6 production | % inhibition of MCP-1 production | % inhibition of MIP-1α production | % inhibition of RANTES production | Mean inhibition |
| KDT501 | No inhibition (NI) | 23 | 49 | 77 | 62 | 77 | 48 |
| KDT100 | NI | NI | <20% | 61 | NI | 22 | <20% |
| KDT700 | <20% | NI | <20% | 88 | 36 | 64 | 34 |
| KDT0005 | NI | NI | <20% | 38 | 20 | 25 | <20% |
| KDT0017 | NI | <20% | 50 | 80 | NI | NI | 23 |
| KDT0020 | 75 | <20% | 70 | 82 | <20% | 35 | 46 |
| KDT0024 | 81 | 27 | 53 | 80 | NI | 20 | 44 |
| KDT0033 | 87 | 68 | 87 | 100 | 95 | 97 | 89 |
| KDT0034 | 87 | 65 | 84 | 100 | 94 | 98 | 88 |
| KDT0035 | 89 | 44 | 65 | 95 | 82 | 84 | 77 |
| KDT0036 | 45 | 97 | 83 | 98 | 25 | 88 | 73 |
| KDT0037 | 82 | 87 | 61 | 98 | 22 | 83 | 72 |
| KDT0038 | NI | NI | NI | 46 | NI | <20% | <20% |
| KDT0039 | NI | <20% | 22 | 50 | 23 | 58 | 26 |
| KDT0040 | 54 | 26 | NI | 53 | NI | 18 | 25 |
| KDT0001/2 | 55 | NI | 60 | 74 | <20% | 45 | 39 |
| Rosiglitazone (10 μM) | NI | 6 | NI | NI | NI | 24 | <20% | high level expression of PPARα, or PPARγ and containing a luciferase report gene specific to the appropriate PPAR. Following activation by agonist binding, PPAR induces expression of the luciferase reporter gene. Luciferase activity therefore provides a surrogate for measuring PPAR activity in agonist-treated cells.

Reporter cells were plated on a 96-well plate at 100 µL per well, and 100 µL of KDT test compounds (50, 25, 12.5, 6.25, 3.13, 1.56 µM) were added to each well in duplicates. For the PPARγ assay, rosiglitazone (1000, 500, 250, 125, 62.5, and 31.25 nM) was used as a positive control. For the PPARα assay, GW590735 (5000, 1670, 560, 185, 62 and 21 nM) was used as a positive control. 0.1% DMSO was used as a solvent control for each assay. Plates were incubated for 20 hours in a humidified incubator at 37° C. and 5% CO$_2$. After incubation, the cell medium was discarded and the cells were treated with 100 µL of luciferase detection reagent for 15 minutes. Plates were analyzed using a luminometer (Victor2, Perkin Elmer). Average relative light unit (RLU) and standard deviation were measured.

Results are summarized in Table 3, with data reported as % level of PPARγ activity compared to rosiglitazone (500 nM) or PPARα activity compared to GW590735 (21 nM).

| Test compound (12.5 µM) | PPARα % GW590735 (20.6 nM) | PPARγ % rosiglitazone (500 nM) |
| --- | --- | --- |
| KDT501 | <5 | 31 |
| KDT100 | <5 | 23 |
| KDT700 | <5 | <5 |
| KDT0005 | <5 | <5 |
| KDT0017 | <5 | <5 |
| KDT0020 | <5 | <5 |
| KDT0024 | <5 | <5 |
| KDT0033 | <5 | 10 |
| KDT0034 | 9 | 5 |
| KDT0035 | 40 | 43 |
| KDT0036 | <5 | 8 |
| KDT0037 | <5 | 34 |
| KDT0038 | <5 | <5 |
| KDT0039 | <5 | <5 |
| KDT0040 | <5 | <5 |
| KDT0001/2 | <5 | <5 |

As expected, rosiglitazone and GW590735 increased the activity of PPARγ and PPARα, respectively. Four of the THIAA derivatives (KDT100, KDT0033, KDT0036, and KDT0037) increased PPARγ activity by 5% or greater in a manner consistent with their activity as partial PPARγ agonists while exhibiting no effect on PPARα activity, suggesting that these compounds are specific PPARγ agonists. Unexpectedly, KDT0034 and KDT0035 were found to act as dual PPARα and PPARγ agonists.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Berge J Pharm Sci 66:1 (1977)
2. Dahlberg J Sep Sci 33:2828 (2010)
3. Dahlberg J Sep Sci 35:1183 (2012)
4. Desai Inflamm Res 58:229 (2009)
5. Everard PLoS One 7:e33858 (2012)
6. Hall Phytochem 69:1534 (2009)
7. Khatib Food Chem 119:354 (2010)
8. Konda Arthritis Rheum 62:1683 (2010)
9. Ting J Am Soc Brew Chem 54:103 (1996)
10. Tripp Acta Hort (ISHS) 848:221 (2009)

What is claimed is:

1. A tetrahydro-iso-alpha acid (THIAA) derivative selected from the group consisting of (4R,5R)-3,4-dihydroxy-4-(1-hydroxy-4-methylpentyl)-2-(N-methoxy-3-methylbutanimidoyl)-5-(3-methylbutyl)cyclopent-2-en-1-one (KDT0005), (4R,5R)-4-hydroxy-2-{1-[(2-hydroxyethyl)amino]-3-methylbutylidene}-5-(3-methylbutyl)-4-(4-methylpentanoyl)cyclopentane-1,3-dione (KDT0017), (4R,5R)-4-hydroxy-5-(3-methylbutyl)-2-[3-methyl-1-(methylamino)butylidene]-4-(4-methylpentanoyl)cyclopentane-1,3-dione (KDT0020), (4R,5R)-2-[1-(benzylamino)-3-methylbutylidene]-4-hydroxy-5-(3-methylbutyl)-4-(4-methylpentanoyl)cyclopentane-1,3-dione (KDT0024), (1S,5R)-2-hydroxy-3-(3-methylbutanoyl)-5-(3-methylbutyl)-1-(4-methylpentanoyl)-4-oxocyclopent-2-en-1-yl 2,2-dimethylpropanoate (KDT0033), (1S,5R)-2-hydroxy-3-(3-methylbutanoyl)-5-(3-methylbutyl)-1-(4-methylpentanoyl)-4-oxocyclopent-2-en-1-yl 3,3-dimethylbutanoate (KDT0034), but-3-yn-1-yl(1S,5R)-2-hydroxy-3-(3-methylbutanoyl)-5-(3-methylbutyl)-1-(4-methylpentanoyl)-4-oxocyclopent-2-en-1-yl carbonate (KDT0035), (1S,5R)-2-hydroxy-5-(3-methylbutyl)-1-(4-methylpentanoyl)-3-(2-methylpropanoyl)-4-oxocyclopent-2-en-1-yl decanoate (KDT0036), (1S,5R)-2-hydroxy-5-(3-methylbutyl)-1-(4-methylpentanoyl)-3-(2-methylpropanoyl)-4-oxocyclopent-2-en-1-yl 2-methylpropyl carbonate (KDT0037), 5-[(1S,5R)-1,2-dihydroxy-3-(3-methylbutanoyl)-5-(3-methylbutyl)-4-oxocyclopent-2-en-1-yl]-2-methyl-5-oxopentanoic acid (KDT0038), (4R,5R)-3,4-dihydroxy-4-(1-hydroxy-4-methylpentyl)-2-(3-methylbutanoyl)-5-(3-methylbutyl)cyclopent-2-en-1-one (KDT0039), (4S,5R)-3,4-dihydroxy-4-[(2E)-4-hydroxy-4-methylpent-2-enoyl]-2-(3-methylbutanoyl)-5-(3-methylbut-2-en-1-yl)cyclopent-2-en-1-one (KDT0040), (4R,5R)-3,4-dihydroxy-2-(N-methoxy-3-methylbutanimidoyl)-4-(N-methoxy-4-methylpentanimidoyl)-5-(3-methylbutyl)cyclopent-2-en-1-one (KDT0001/2), (1S,5R)-2-hydroxy-5-(3-methylbutyl)-1-(4-methylpentanoyl)-3-(2-methylpropanoyl)-4-oxocyclopent-2-en-1-yl 3,3-dimethylbutanoate (KDT0041), (1S,5R)-2-hydroxy-5-(3-methylbutyl)-1-(4-methylpentanoyl)-3-(2-methylpropanoyl)-4-oxocyclopent-2-en-1-yl benzoate (KDT0042), and (1R,2S)-3-hydroxy-4-(3-methylbutanoyl)-2-(3-methylbutyl)-1-(4-methylpentanoyl)-5-oxocyclopent-3-en-1-yl 2-[4-(2-methylpropyl)phenyl]propanoate (KDT0043), or a salt or crystal thereof.

* * * * *